United States Patent [19]

Corbiere

[11] Patent Number: 5,523,082
[45] Date of Patent: Jun. 4, 1996

[54] PROCESS FOR PRODUCING STABLE PHARMACEUTICAL FORMS OF AN ERGOLINE DERIVATIVE AND THE PHARMACEUTICAL COMPOSITIONS THUS OBTAINED

[76] Inventor: Jerome Corbiere, 17 Rue Cortambert, 75016 Paris, France

[21] Appl. No.: 105,342

[22] Filed: Aug. 9, 1993

[30] Foreign Application Priority Data

Aug. 9, 1991 [FR] France .................. 91 10159

[51] Int. Cl.$^6$ .................. A61K 3/38; A61K 9/08
[52] U.S. Cl. .................. 424/78.04; 424/422
[58] Field of Search .................. 514/438; 424/78.04, 424/422

[56] References Cited

U.S. PATENT DOCUMENTS 4,657,925  4/1987  Horn ..................... 514/438

FOREIGN PATENT DOCUMENTS 2165752  4/1986  United Kingdom .

Primary Examiner—Thurman K. Page
Assistant Examiner—Peter F. Kulkosky
Attorney, Agent, or Firm—Bierman and Muserlian

[57] ABSTRACT

The invention relates to new pharmaceutical compositions intended for administration by ocular route and to the process for obtaining them.

A specific subject of the invention is a process for obtaining pharmaceutical compositions intended for ophthalmic route of which the active ingredient is bromocriptine, in which the active ingredient is dissolved in methanol then this solution is diluted with an aqueous solute containing a hydrosoluble inert filler, the mixture is lyophilized then the lyophilization deposit is redissolved at the time of use in an aqueous solute containing a preservative, a polyethylene glycol, physiological serum and an ethylenic acid.

The solute obtained is a medicament for intra-ocular hypertension.

9 Claims, No Drawings

PROCESS FOR PRODUCING STABLE PHARMACEUTICAL FORMS OF AN ERGOLINE DERIVATIVE AND THE PHARMACEUTICAL COMPOSITIONS THUS OBTAINED

The present invention relates to new pharmaceutical compositions intended for administration by ocular route.

A more particular subject of the invention is new liquid pharmaceutical compositions the active ingredient of which, being very slightly soluble in water, is dispersed in an aqueous vehicle.

A specific subject of the invention is pharmaceutical compositions intended for ophthalmic route in which the active ingredient is a bromocriptine salt and, in particular, bromocriptine methane sulphonate in a form which ensures the stability of the active ingredient and good preservation of the pharmaceutical forms.

The use by ophthalmic route of bromocriptine and of its salts has hitherto come up against a major difficulty which has up to now remained unsolved, which is the easy decomposition of bromocriptine by photolysis or oxidation, leading to isomers in position 9 or 10 as well as epimers in position 8 which lack activity.

Indeed, it is proving to be important to be able to administer, by local route, bromocriptine or one of its salts and, in particular, alpha-bromocriptine which is an agonist of the DA 2 and DA 1 dopaminergic receptors, as well as a blocking agent of the alpha adrenergic receptors. By ocular administration of bromocriptine, the intra-ocular pressure (IOP) is reduced without significantly modifying, at the doses administered, the blood pressure, the diameter of the pupil or the cardiac rhythm. Also, the level of prolactin is only very slightly modified.

This effect cannot be linked with a systemic effect of bromocriptine because in parallel tests, conducted on a single eye, this compound did not significantly modify the intraocular pressure of the contra-lateral eye.

According to Q. MEKKI et al—The Lancet (4 Feb. 1984) p. 287, this action would be linked directly with a stimulating effect on the intra-ocular dopaminergic receptors.

Previously, various solutions were proposed for resolving the technical problem posed by the local administration of an ergoline salt and, in particular, of a bromocriptine salt.

It is thus that D. E. POTTER et al—Fed. Proceed. 41 (1982) 1057 (Abst. 1599) used a solution of bromocriptine in a 5% solution of glucose, insisting on the fact that a rapid instillation was essential in order for the medicament to retain its action.

These same authors then used (Curent Eye Research 3 (2) (1984) 307), either a solution of the mesylate in water, or a basic suspension in Tween 80, but the conclusion of this article is that a new formulation which is better tolerated must be found.

In a subsequent article (The Lancet—4 Feb. 1984) Q. A. MEKKI et al drew attention more particularly to the fact that a solution in a thiomersal/polyvinyl pyrrolidone/10% methane sulphonic acid/sodium chloride mixture showed a lack of tolerance, involving in particular the presence of conjunctival infection in all the patients, perhaps due to the nature of the vehicle.

At the same time, the French Patent 2,571,962 (SANDOZ SA) described and claimed another process for the local administration of bromocriptine which consists of putting bromocriptine mesylate in suspension in distilled water which has had methane sulphonic acid added to it, adding a large quantity of polyvinyl pyrrolidone and finally a solution of benzalkonium chloride to ensure the stability of the solution and to lyophilize the mixture.

The accepted technical solution resided therefore on the one hand in the addition of benzalkonium chloride as stabilizing agent and on the other hand in the lyophilization operation which ensures the preservation and the dispersion of the mixture with a view to an improved resolubilization.

In this embodiment, 2 ml of solution contains 1 mg of bromocriptine but particularly 100 mg of polyvinyl pyrrolidone and 1.05 mg of benzalkonium chloride. In addition, the pH of the reconstituted solution is indicated as being 3.6 which is quite acidic for an ocular preparation and at the limit of tolerance for a normal eye.

The technical problem had therefore not been resolved in a satisfactory manner and consequently it seemed important to find another solution, significantly different from those previously described and substantially improved relative to the latter.

It is on this solution that the invention, which is the subject of the present Patent Application, is based.

The embodiment according to the invention consists of dissolving bromocriptine or one of its addition salts in the minimum quantity of methanol, diluting this solution with a mixture of water and polyvinyl pyrrolidone which has had an inert filler, soluble in this medium, added to it, lyophilizing this mixture and redissolving the lyophilization deposit at the time of use in a solution formed by polyethylene glycol, physiological serum, a preservative and an ethylenic acid.

This effect is without any doubt surprising. In fact, previous studies such as those by Mack (J. Pharm. Sci. 52, (1963) 694), by SWARBRICK (J. Pharm. Sci. 54 (1965) 1229) and by N. E. WEBB (Bull. Parenteral Drug Assoc. 30, (1976) 180) had underlined the importance of the pharmaceutical problem posed by the use of hydrophobic substances and by the difficulty of making them apparently soluble in water.

The solubilization process that these authors had employed generally used the formation of micells or used mixed solvents in which the active ingredient is capable of dissolving. Certain ionizable derivatives are very easily hydrolyzable (basic salts or salts of weak acids) or have a pH incompatible with parenteral administration (very acid or very alkaline solutions). That is why SWARBRICK had described a general method for dissolving in an aqueous system which consists of dispersing the active ingredient in the form of micells using ionic or non-ionic surfactants. Neverthless, this system had two major disadvantages. On the one hand, the active ingredient may be altered or hydrolyzed more rapidly than in systems in which it is insoluble. On the other hand, the active ingredient loses part of its biological activity either by modification of its resorption rate, or because the micells carry an electric charge which modifies their capacity for bonding with the receptor site.

It is in this way, for example, that the phenolic antibacterials lose their activity following interaction with anionic surfactants.

That is why, even if the micell formation system enables hydrophobic compounds to become soluble in water, it does not resolve the general pharmaceutical problem of administration of an active ingredient whose activity, stability or penetration in the organism is maintained or even improved relative to the insoluble form.

The concentration of bromocriptine or one of its salts in the diluted solution may vary by significant proportions ranging from 1 mg to 1 g % of solution. In a preferred manner, the content of active ingredient is comprised between 0.15 and 0.5% of the final solution.

In the process according to the invention, an addition salt of bromocriptine is preferably used such as for example the hydrochloride or in particular the methane sulphonate which is slightly more soluble in water.

The polyvinyl pyrrolidone used is a slightly viscous, liquid polyvinyl pyrrolidone such as polymers with a molecular weight ranging from 10,000 to 25,000. The inert filler soluble in the medium can be a polyol such as mannitol or sorbitol but the product which forms a stable deposit most easily after lyophilization is urea.

The dissolution of bromocriptine or one of its salts must use the minimum quantity of methanol because the lyophilization of an aqueous solution of methanol is difficult and might well be incomplete.

In the form of a lyophilizate, bromocriptine keeps perfectly and undergoes almost no chemical degradation.

In order to redissolve bromocriptine, an aqueous solvent is used containing polyethylene glycol and preferably polyethylene glycol 200, polyethylene glycol 300 or polyethylene glycol 400. An ethylenic acid is also added which contributes to the stability of the bromocriptine once it has been solubilized. A suitable ethylenic acid is an alpha-ethylenic acid and in particular maleic acid. Other ethylenic acids produce encouraging results but maleic acid enables the solution, after it has been reconstituted, to be kept almost without degradation for 15 days at ambient temperature.

The preservative added to the redissolution solvent is preferably a quaternary ammonium salt soluble in water such as for example dodecinium bromide, ketylpyridinium chloride or benzalkonium chloride.

The concentration of preservative is small and ranges between 5 and 15 mg of product per 100 ml.

Alpha-ethylenic acid is also present in small quantities as a function of its solubility in water. An effective concentration ranges between 10 and 50 mg % by volume.

The reconstituted concentration is perfectly stable under normal storage conditions and can be diluted subsequently with a saline or non-saline aqueous vehicle, without risk of recrystallization, precipitation or chemical alteration.

The redissolution solution or solvent can also have a thickener added to it.

The thickener that can be introduced into the aqueous phase is a chemical derivative of cellulose such as methylcellulose, ethylcellulose, hydroxypropyl cellulose, hydroxypropylmethyl cellulose, carboxymethyl cellulose or crosslinked carboxymethyl cellulose (croscarmellose).

The pharmaceutical compositions according to the invention can be used as a dopaminergic agent, in particular for the treatment of open-angle glaucoma.

The posology is 1 to 4 drops of solution in the eye to be treated at a rate of one to three administrations per day.

The following examples illustrate the invention without however limiting it.

EXAMPLE 1

EYE WASH WITH BROMOCRIPTINE 13.3 g of bromocriptine methane sulphonate is dissolved in 0.5 l of methanol by agitating at 0° C. shaded from the light. Then a solution of 65 g of polyvinyl pyrrolidone and 65 g of urea in 9.5 l of distilled water is added.

After agitation, the solution is perfectly homogeneous. The pH of the solution is clearly acid. Determination of bromocriptinine (degradation product of bromocriptine) indicates a content of less than 0.5. The solution is distributed into 1 ml flasks and is lyophilized.

Then a redissolution solute is prepared formed by:

| | |
|---|---|
| polyethylene glycol 400 | 1.5 g |
| physiological serum | 8.5 g |
| benzalkonium chloride | 1 mg |
| maleic acid | 2 mg |

This solute is distributed into 10 ml ampoules and heat-sterilized.

Each ampoule is intended for the redissolution of lyophilization deposit.

EXAMPLE II

RECONSTITUTION SOLUTION

| | |
|---|---|
| polyethylene glycol 400 | 1 g |
| physiological serum | 9 g |
| benzalkonium chloride | 1 mg |
| ascorbic acid | 10 mg | for redissolving a lyophilizate

EXAMPLE III

RECONSTITUTION SOLUTION

| | |
|---|---|
| polyethylene glycol 400 | 1.5 g |
| physiological serum | 8.5 g |
| benzalkonium chloride | 1 mg |
| ascorbic acid | 10 mg | for redissolving a lyophilizate

EXAMPLE IV

RECONSTITUTION SOLUTION

| | |
|---|---|
| polyethylene glycol 400 | 1.5 g |
| physiological serum | 8.5 g |
| benzalkonium chloride | 1 mg |
| maleic acid | 1.38 mg | for dissolving a lyophilizate

EXAMPLE V

RECONSTITUTION SOLUTION

| | |
|---|---|
| polyethylene glycol 400 | 1 g |
| physiological serum | 9 g |
| benzalkonium chloride | 1 mg |
| maleic acid | 1.1 mg | for dissolving a lyophilizate

EXAMPLE VI

| | |
|---|---|
| polyethylene glycol 400 | 1.5 g |
| physiological serum | 8.5 g |

-continued

| benzalkonium chloride | 1 mg |
| maleic acid | 1.6 mg | for dissolving a lyophilizate

EXAMPLE VII

RECONSTITUTION SOLUTION

| polyethylene glycol 400 | 1.5 g |
| physiological serum | 8.5 g |
| benzalkonium chloride | 1 mg |
| acrylic acid polymer marketed under the mark Carbopol 940 | 1.5 mg | for dissolving a lyophilizate

EXAMPLE VIII

RECONSTITUTION SOLUTION

| polyethylene glycol 400 | 1.5 g |
| physiological serum | 8.5 g |
| benzalkonium chloride | 1 mg |
| maleic acid | 1.3 mg | for dissolving a lyophilizate

EXAMPLE IX

RECONSTITUTION SOLUTION

| polyethylene glycol 400 | 1.5 g |
| physiological serum | 8.5 g |
| benzalkonium chloride | 1 mg |
| maleic acid | 1.4 mg | for dissolving a lyophilizate

EXAMPLE X

RECONSTITUTION SOLUTION

| polyethylene glycol 400 | 1.5 g |
| physiological serum | 8.5 g |
| benzalkonium chloride | 1 mg |
| maleic acid | 1.5 mg | for dissolving a lyophilizate

EXAMPLE XI

RECONSTITUTION SOLUTION

| polyethylene glycol 400 | 1.5 g |
| physiological serum | 8.5 g |
| benzalkonium chloride | 1 mg |
| maleic acid | 1.6 mg | for dissolving a lyophilizate

EXAMPLE XII

RECONSTITUTION SOLUTION

| polyethylene glycol 400 | 1.5 g |
| physiological serum | 8.5 g |
| benzalkonium chloride | 1 mg |
| fumaric acid | 1 mg | for dissolving a lyophilizate

Verification of the stability of the reconstituted solutions (bromocriptinine content)

See Table below.

| Tests | pH | $D_0$ | $D_2$ | $D_3$ | $D_4$ | $D_5$ | $D_{10}$ | $D_{11}$ | $D_{13}$ | $D_{14}$ | $D_{15}$ | $D_{17}$ |
|---|---|---|---|---|---|---|---|---|---|---|---|---|
| Solute 1 | 3.6 | 0.32 | | 2.57 | | 4.36 | | | | | | 6.30 |
| Solute 2 | 3.75 | 0.30 | | 2.89 | | 5.33 | | | | | | 10.44 |
| Solute 3 | 3.2 | 0.31 | | 0.53 | | 2.03 | | | | | | 3.79 |
| Solute 4 | 3.1 | 0.28 | | 0.52 | | 1.96 | | | | | | 3.32 |
| Solute 5 | 4.0 | | 1.95 | | | | | | | 5.82 | | 8.00 |
| Solute 6 | 4.0 | | 2.16 | | | | | | | 7.99 | | 9.48 |
| Solute 7 | 3.8 | | | | | | 4.49 | | 5.06 | | | 6.43 |

It is therefore noted that the reconstituted bromocriptine solution keeps in a very satisfactory manner and that for certain tests, degradation is practically negligible.

Alteration of the product is shown by the formation of not very soluble bromocriptinine which can lead to the formation of a deposit when this product is in larger quantities.

The degree of preservation is a function of the pH value of the reconstituted solution and of the concentration of ethylenic acid.

I claim:

1. A process for the preparation of a stable ophthalmic composition of bromocriptine or a pharmaceutically acceptable salt thereof consisting essentially of dissolving bromocriptine or a pharmaceutically acceptable salt thereof in a minimum of methanol, diluting the resulting solution with a mixture of water, polyvinyl pyrrolidone and an inert filler soluble therein, lyophilizing the resulting mixture and redissolving the lyophilization deposit in a solution of polyethylene glycol, physiological serum, preservative and an ethylenic acid to obtain a clear stable solution which can be stored.

2. An ophthalmic composition produced by the process of claim 1.

3. A process according to claim 1 in which the preservative is a quaternary ammonium salt.

4. A process according to claim 1 in which the ethylenic acid is an alpha-ethylenic acid.

5. A process according to claim 1 in which the ethylenic acid is maleic acid or fumaric acid.

6. A process according to claim 1 in which the concentration of bromocriptine or one of its salts in the final solution varies from 1 mg to 1 g %.

7. A process according to claim 1 in which the content of active ingredient is comprised between 0.15 and 0.5% in the final solution.

8. A process according to claim 1 in which the inert filler is constituted by mannitol, sorbitol and/or urea.

9. A process according to claim 1 in which the pH of the final solution is comprised between 3.5 and 4.5.

* * * * *